(12) United States Patent
Saluja et al.

(10) Patent No.: US 9,139,883 B2
(45) Date of Patent: Sep. 22, 2015

(54) **PCR-BASED DETECTION METHOD FOR *CHLAMYDIA TRACHOMATIS***

(75) Inventors: Daman Saluja, New Delhi (IN); Uma Chaudhury, New Delhi (IN); Mashook Ali, New Delhi (IN)

(73) Assignees: University of Delhi (IN); The Secretary, Department of Biotechnology (IN)

( * ) Notice: Subject to any disclaimer, the term of this patent is extended or adjusted under 35 U.S.C. 154(b) by 820 days.

(21) Appl. No.: 13/220,268

(22) Filed: Aug. 29, 2011

(65) Prior Publication Data
US 2012/0010089 A1    Jan. 12, 2012

Related U.S. Application Data

(63) Continuation-in-part of application No. 12/064,143, filed as application No. PCT/IN2006/000282 on Aug. 7, 2006, now abandoned.

(30) Foreign Application Priority Data

Aug. 17, 2005 (IN) .............................. 1589DEL/2005

(51) Int. Cl.
*C12P 19/34* (2006.01)
*C12Q 1/68* (2006.01)

(52) U.S. Cl.
CPC ............ *C12Q 1/689* (2013.01); *C12Q 2600/16* (2013.01)

(58) Field of Classification Search
None
See application file for complete search history.

(56) References Cited

U.S. PATENT DOCUMENTS

2006/0246447 A1    11/2006    Inose et al.

FOREIGN PATENT DOCUMENTS

WO          9811259 A2      3/1998
WO       2004076694 A1      9/2004

OTHER PUBLICATIONS

Richard S. Stephens, et al., "Genome Sequence of an Obligate Intracellular Pathogan of Humans: *Chlamydia trachomatis*", Science, Oct. 1998, pp. 754-759, vol. 282.
Sophie Dessus-Babus et al, "Sequencing of Gyrase and Topoisomerase IV Quinolone-Resistance-Determining Regions of *Chlamydia trachomatis* and Characterization of Quinolone-Resistant Mutants Obtained In Vitro", Antimicrobial Agents and Chemotherapy, Oct. 1998, pp. 2474-2481, vol. 42, No. 10.
Shigeaki Yokoi et al.: "Uncommon occurence of fluoroquinolone resitance-associated alternations in GyrA and ParC in clinical strains of *Chlamydia trachomatis*"; J. Infect. Chemother., 2004; pp. 262-267., vol. 10.

*Primary Examiner* — Suchira Pande
(74) *Attorney, Agent, or Firm* — The Webb Law Firm

(57) ABSTRACT

A process for designing of PCR-based detection method for *Chlamydia trachomatis* comprising designing of PCR primers from the genome sequence of *Chlamydia trachomatis* selecting DNA sequence of genes for PCR based diagnostic of *Chlamydia trachomatis*, optimizing the PCR conditions of the PCR primers; subjecting the said genes and primers to the step of characterization.

8 Claims, No Drawings

PCR-BASED DETECTION METHOD FOR *CHLAMYDIA TRACHOMATIS*

CROSS REFERENCE TO RELATED APPLICATIONS

This is a Continuation-In-Part of U.S. patent application Ser. No. 12/064,143, filed Sep. 17, 2008, which is a National Stage application of International Patent Application No. PCT/IN2006/000282, filed Aug. 7, 2006, which in turn claims the benefit under 35 U.S.C. §119 of Indian Patent Application No. 1589DEL/2005, filed Aug. 17, 2005, each of which is incorporated herein by reference in its entirety.

The Sequence Listing associated with this application is filed in electronic format via EFS-Web and is hereby incorporated by reference into the specification in its entirety. The name of the text file containing the Sequence Listing is 4544-113164_ST25.txt. The size of the text file is 2,323 KB, and the text file was created on Aug. 29, 2011.

BACKGROUND

This invention relates to a designing of PCR based detection method for *chlamydia trachomatis*.

Culture method: Chlamydiae were first detected by light microscopy in conjuctival scrapings from orangutangs inoculated with material from trachoma patients in 1907. The diagnostic sensitivity and specificity of light microscopy, however, are not satisfactory. Because *Chlamydia* depends on ATP and other nutritional factors from a host cell it can reproduce only in other cell. The inclusion body, containing thousands of *C. trachomatis* can be visualized by staining with fluorescein-conjugated antibody directed against one of the organism's surface antigens. Because the inclusion body is highly characteristic, cell culture is considered to have a specificity of 100%.

Sensitivity of this method is as low as 50% as organisms may lose infectivity during transportation and storage, which will reduce the likelihood of propagation. In addition, the surface area of the cell culture layer and/or the amount of sample material added to the cell culture influence the sensitivity. Cell culture, however, is time-consuming, laborious and expensive and can therefore be provided by only a few central laboratories.

Antigen detection: Antigen detection methods comprise Enzyme-inked immunosorbent assays (ELISA) and Direct immunofluorescence assays (DFA). The currently commercially available ELISA all use the LPS as antigen. The LPS part of *Chlamydia* binds to immobilized anti-LPS antibodies and the ELISA tests are therefore genus specific and detect all *Chlamydia* species. A secondary antibody that is bound to the *Chlamydia* is linked to an enzyme, which generates a colour change, measured as optical density, on addition of subtrate. In DFA, fluorescein-conjugated antibodies directed against either the LPS or the MOMP component react with the *Chlamydia* surface. The fluorescein can subsequently be visualized by fluorescence microscopy.

The diagnostic efficacy of these methods is not high enough to warrant clinical use unless the need for a fast result overweighs the lower diagnostic accuracy. Also, the ELISA tests may reveal positive results in the presence of other organisms such as *E. coli* and *Bacteroides* sp, and *Staphylococcus aureus* may be captured instead of *Chlamydia* due to binding to the Fc region of the antibodies, thereby causing false-positive reactions. DFA requires skilled personnel in order to differentiate *C. trachomatis* organisms from non-specific fluorescent particles.

DNA/RNA detection: DNA/RNA detection assays can be divided into probe assays and amplification assays. In probe assays a synthesized single stranded oligonucleotide hybridizes to a part of *C. trachomatis* DNA or RNA. The most widely used probe technique is the Gen-Probe assay, in which a probe reacts with ribosomal RNA (rRNA) of *C. trachomatis*, which is present in hundreds of copies in each organism.

The diagnostic performance of non-amplified probe technique is not substantially different from that of the best ELISA.

Nucleic acid amplification tests (NAATs): In nucleic acid amplification Tests specific probes hybridize to *C. trachomatis* DNA or RNA and the DNA/RNA flanked by the primers (target DNA) is exponentially copied. Target gene—The Plasmid: The plasmid is unique for *C. trachomatis*, is well conserved within the species, and is present in approximately 10 copies in each *C. trachomatis* organism. Using the plasmid as target DNA should therefore theoretically lower the detection limit by a factor of 10 compared with a single chromosomal gene, for example MOMP gene.

The 16S-rRNA gene: By using the 16S-rRNA gene, which is present in all bacteria and is the most conserved gene known, all *Chlamydia* species can be detected by just one primer set. This is done by constructing the primers to anneal at the genus-specific regions of the 16S-rRNA gene. The genus specific regions flank variable-regions that are specific for each species. The amplified products comprise the variable region flanked by the two genus specific regions. The species can be determined by specific probe or RFLP, or by DNA sequencing.

Target gene for NAATs Target gene for NAATs The Plasmid: Some studies give evidence or suggest that the plasmid-free variants are present in clinical samples, and although it may seem that plasmid is involved in DNA replication, it has been possible to culture a plasmid-free variant. Thus, the infections caused by plasmid-free variants will be undetected if the plasmid is used as target gene.

The 16S-rRNA gene: Due to high homology of the 16S RNA gene with other organisms, optimal reaction conditions are crucial in order to avoid annealing of primers to 16S-rRNA gene of the other organisms that are present in all non-sterile clinical samples.

OBJECTS OF THE INVENTION

An object of this invention is to propose a designing of PCR-based detection method for *Chlamydia trachomatis*.

Another object of this invention is to propose identification of unique sequences in the genome of *C. trachomatis*.

Further object of this invention is to propose a designing of PCR-based diagnostic method for *Chlamydia trachomatis*.

Still further object of this invention is to propose a multplex PCR based detection method for *Chlamydia trachomatis* and *Neisseria gonorrhoeae*.

BRIEF DESCRIPTION OF THIS INVENTION

According to this invention there is provided a process for designing of PCR-based detection method for *Chlamydia trachomatis* comprising designing of PCR primers from the genome sequence of *C. trachomatis* selecting DNA sequence of genes for PCR based diagnostic of *C. trachomatis*, optimizing the PCR conditions of the PCR primers; subjecting the said genes and primers to the step of characterization.

Primers for use in identification of *C. trachomatis* in a biological sample are provided, including one or more oligonucleotide primers selected from the group consisting of SEQ ID NOS: 1-4.

Methods of detecting *Chlamydia trachomatis* in a sample, such as a clinical or patient sample, comprising: conducting a PCR assay using oligonucleotide primers for *Chlamydia trachomatis* GyrA gene and optionally a *Chlamydia trachomatis* phospholipase D endonuclease gene; wherein the oligonucleotide primers selectively amplify a portion of the *Chlamydia trachomatis* GyrA gene, and optionally a *Chlamydia trachomatis* phospholipase D endonuclease gene.

DETAILED DESCRIPTION OF THIS INVENTION

Designing of PCR Primers:

The key to any polymerase chain reaction is a pair of oligonucleotide primers of defined sequence. Primers were designed using the GENEFISHER program from the web site www.ebl.ac.uk. From the genome sequence of *C. trachomatis* available on the medline, the DNA sequence of those genes, which appear to be unique to *C. trachomatis*, were selected using Blast. For *C. trachomatis* DNA sequences of two genes were selected for PCR based diagnostic method. These were gyrA genes, phospholipase D endonuclease superfamily gene (PHA).

Optimization of the PCR Conditions:

For initial standardization of our PCR assays to be used in a clinical setting, various experiments were performed with authentic DNA as template and the data was confirmed by using the patient samples.

Characterization of the PCR Amplified Product:

The authenticity of the amplified products was established by sequencing of the amplified products. The amplified gene products were purified from the gel, sequenced and nucleotide sequence obtained was matched with that of the known DNA sequence in the Public domain. Complete identity in sequence was observed for both amplified products with their respective genes.

Comparison of the Specificity of the PCR Assays Using the GyrA Primers for *Chlamydia trachomatis:*

In order to select one or two primer pair set that could be used routinely for pre-clinical evaluation we tested the specificity of each primer pair. To evaluate the specificity of the selected primers, DNA extracted from several positive clinical isolates of *Chlamydia trachomatis*, six non-gonococcal *Neisseria* species, three genital commensals and four *N. gonorrhoeae* isolates as well as *C. albicans, C. glabrata, Herpes simplex, Mycoplasma* etc. were used as templates.

Development of a Multiplex-PCR Assay to Detect *C. trachomatis:*

To increase the specificity our PCR based diagnostic system we developed multiplex PCR assay using gyrA and PHA primers. Initial standardization for multiplex PCR was done using authentic DNA as well as with known positive samples. The method was then extended to the clinical samples. All assays were compared with simple PCR for the two genes separately. Concentration of dNTPs used was 300 μM, Taq DNA polymerase was used 1.25 U. First ten cycles were run with gyrA primers and then PHA primers were added for the following 28 cycles.

Primers:

PHA —generates 368 bp amplicon product.

```
                              (SEQ ID NO: 1)
5'- TCTTTTTAAACCTCCGGAACCCACTT -3'

(SEQ ID NO: 2)
5'- GGATGGCATCGCATAGCATTCTTTG -3'
```

Exemplary PHA amplicon product (SEQ ID NO: 5):

```
5'- TCTTTTTAAA CCTCCGGAAC CCACTTCTTC CACAGATTCT
TCTAAAGAAC CTCCTAAAGA ATCTGCATGG AAAGTAGTCT
CTCATTCTCG AGGACGCCGT CGCGCTCGAT CCAACCCCTC
CCCTCACACA TCTCAAAATA CTCCTTCTCC AAAAGACTCT
TCTTTAGTTG CTCGTACGGA TAAAGCGGCA ACAGATATCT
TTAATTCGGC TAAACACAAA GCGATTGAAA CGACAAAAAG
AAGTGATCAG CAAAGCAGAT CCTTACATAT ACTGCACCTT
TTAGCTGAAA ATCCGGAACC CATTGTGTTC CACTCAGCTC
ACCAAACAAA CCACAACGAT CCGCAAAGAA TGCTATGCGA
TGCCATCC -3'
```

GyrA—generates 462 bp amplicon product.

```
                              (SEQ ID NO: 3)
5'- CCTGATGCTAGGGACGGATT -3'

(SEQ ID NO: 4)
5'- CCCTAAATTATGCGGTGGAAT -3'
```

Exemplary GyrA amplicon product (SEQ ID NO: 6).

```
5'- CCTGATGCTA GGGACGGATT AAAACCTTCT CAGCGACGTA
TTTTATACGC TATGAAACAA TTAAATCTGA CTCCAGGAGT
AAAGCACAGA AAATGCGCAA AAATTTGCGG TGATACTTCC
GGAGATTATC ACCCTCATGG AGAAAGTGTC ATTTATCCTA
CTTTAGTAAG GATGGCACAG GATTGGGCCA TGCGATACCC
TCTTGTTGAT GGTCAAGGGA ATTTTGGATC CATCGACGGG
GATCCAGCTG CTGCCATGCG ATATACAGAG GCTCGCCTGA
CTCACAGCGC TATCTTTTTG TTAGAGGACC TAGATAAAGA
TACTGTAGAT ATGGTCCCTA ACTACGATGA AACTAAATAT
GAACCTGTAG TTTTTCCTTC AAAATTCCCC AATTTACTTT
GTAATGGCTC CTCAGGCATC GCGGTAGGGA TGGCAACAAA
TATTCCACCG CATAATTTAG GG -3'
```

The designed primers will be used for the diagnosis of *Chlamydia trachomatis* in patient samples. Further, multiplex PCR has been developed for *Chlamydia trachomatis* and *Neisseria gonorrhoeae*, another STD causing organism which co infects the patients. Presently Various other methods like ELISA, DFA, Culture have been used for the diagnosis of *Chlamydia trachomatis* which are not very sensitive as compared to PCR. PCR of 517 by region of plasmid DNA have been used for the diagnosis of *Chlamydia trachomatis*, but it is not of much advantage for the diagnosis, as plasmid is not found in all the strains of *Chlamydia trachomatis*, so it cannot be detected in the samples, which are *Chlamydia* positive but lacking plasmid.

EXAMPLE 1

Standardization of Large Scale Collection of Test Sample

Processing of Clinical Specimens (Urethral Swabs) for DNA Amplification:

The endogenous inhibitors present in the clinical sample that can interfere with nucleic acid amplification influence the performance of PCR testing with the urogenital specimens. A transport medium/collection medium was designed that would remove or neutralize the inhibitors present in the clinical sample. This also helped in the collection of large number of samples.

400 µl sample of specimen was centrifuged for 30 min at 14,000.times.g, and the pellet was treated with 40 µl of lysis buffer (50 mM Tris-HCl [pH 7.5], 1% Triton X-100, 1 mM EDTA, 400 µg of proteinase K per ml). After incubation at 37° C. for 1 h, the lysates were boiled for 10 min and centrifuged briefly. From each lysate, 10 µl was added to 40 µl of PCR mixture.

Detection of Chlamydia trachomatis Using PCR Based Assays:

We have designed two pairs of primers based on the sequence of Chlamydia trachomatis available on net. The PCR conditions using each primer pair have been standardized. In order to select one or two primer pair set that could be used for pre-clinical evaluation it is necessary to test the specificity of each primer pair. This is necessary so as to avoid false negatives. We have standardized gyrA primer to be used for clinical evaluation. Second confirmatory test is being done using PRPHA primer or multiplex PCR using both the sets of primers.

EXAMPLE 2

Development of a Multiplex-PCR Assay for Simultaneous Detection of N. gonorrhoeae and C. trachomatis in the Urogenital Specimens Since Chlamydia trachomatis often co-infects with N. gonorrhoeae and signs and symptoms of the disease are similar to that of gonorrhoea. To check for this coinfecting microorganism in the clinical specimens, we performed a multiplex PCR assay to detect the two organisms simultaneously. For this multiplex PCR assay, the 23S rRNA gene was selected for detecting N. gonorrhoeae and the gyrA gene of the C. trachomatis was used as the target. Conditions for the multiplex-PCR were standardized after testing the samples individually and then in a multiplex assay using authentic clinical samples. When tested individually for N. gonorrhoeae and C. trachomatis, out of the 225 specimens tested, only 17 tested positive for C. trachomatis and 204 tested positive for N. gonorrhoeae (see Table 2). Similar results were obtained using the multiplex PCR assay. Of the seventeen specimens, which were found positive for C. trachomatis, three specimens were also infected with N. gonorrhoeae. It is pertinent to mention that the conditions for multiplex PCR need to be standardized separately as the primers may not amplify with same efficiency when tested together than when tested separately. Moreover, the two co infecting organisms may not be present in the same amount. We found that the concentrations of the four dNTPs when increased from 200 to 300 µM and when the amount of Taq DNA polymerase was increased from 1.5 U to 3 U, better multiplex-PCR results were obtained. Ten cycles were first run with the primer set CT2A and CT2B to increase the number of available templates and hence competitiveness for the subsequent cycles. This was then followed by a further thirty cycles after the addition of the 23S rRNA primer set.

TABLE 2

Comparison of single and Multiplex-PCR results for the detection of Chlamydia trachomatis and Neisseria gonorrhoeae in 225 urogenital specimens

| | Results | | | |
|---|---|---|---|---|
| | | | Multiplex-PCR | |
| | C. trachomatis-PCR | N. gonorrhoeae-PCR | C. trachomatis-PCR | N. gonorrhoeae-PCR |
| Specimen # | | | | |
| 201 | − | + | − | + |
| 7 Multiplexing | − | − | − | − |
| 14 | + | − | + | − |
| 3 | + | + | + | + |

We claim:

1. A multiplex method of detecting *Chlamydia trachomatis* in a sample, comprising: conducting a PCR assay using at least one first oligonucleotide primer for *Chlamydia trachomatis* GyrA gene; wherein the at least one first oligonucleotide primer selectively amplifies a portion of the *Chlamydia trachomatis* GyrA gene; and at least one second oligonucleotide primer for *Chlamydia trachomatis* Phospholipase D endonuclease gene; wherein the at least one second primer selectively amplifies a portion of *Chlamydia trachomatis* phospholipase D endonuclease gene, and wherein the at least one first oligonucleotide primer is selected from the group consisting of SEQ ID NOs: 3-4 and the at least one second oligonucleotide primer is selected from the group consisting of SEQ ID NOs: 1-2.

2. The method according to claim 1, wherein the at least one first oligonucleotide primer of GyrA is SEQ ID NO: 4.

3. The method according to claim 1, wherein the at least one first oligonucleotide primer of GyrA is SEQ ID NO: 3.

4. The method according to claim 1, where in the at least one first oligonucleotide primer of GyrA is at least two first oligonucleotide primers.

5. The method according to claim 1, wherein the at least one second oligonucleotide primer of phospholipase D endonuclease is SEQ ID NO: 1.

6. The method according to claim 1, wherein the at least one second oligonucleotide primer of phospholipase D endonuclease is SEQ ID NO: 2.

7. The method according to claim 1, wherein the at least one second oligonucleotide primer of phospholipase D endonuclease is at least two second oligonucleotide primers.

8. The method according to claim 1, wherein the at least one first oligonucleotide primers are SEQ ID NOs: 3 and 4 and the at least one second oligonucleotide primers are SEQ ID NOs: 1 and 2.

* * * * *

UNITED STATES PATENT AND TRADEMARK OFFICE
CERTIFICATE OF CORRECTION

Page 1 of 1

PATENT NO.         : 9,139,883 B2
APPLICATION NO.    : 13/220268
DATED              : September 22, 2015
INVENTOR(S)        : Daman Saluja et al.

It is certified that error appears in the above-identified patent and that said Letters Patent is hereby corrected as shown below:

In the Claims
Column 10, Line 1, Claim 4, delete "where in" and insert -- wherein --

Signed and Sealed this
Twenty-third Day of February, 2016

Michelle K. Lee
*Director of the United States Patent and Trademark Office*

SEQUENCE LISTING

<160> NUMBER OF SEQ ID NOS: 6

<210> SEQ ID NO 1
<211> LENGTH: 26
<212> TYPE: DNA
<213> ORGANISM: Chlamydia trachomatis

<400> SEQUENCE: 1 tcttttaaa cctccggaac ccactt        26

```
<210> SEQ ID NO 2
<211> LENGTH: 25
<212> TYPE: DNA
<213> ORGANISM: Chlamydia trachomatis

<400> SEQUENCE: 2
ggatggcatc gcatagcatt ctttg                                          25

<210> SEQ ID NO 3
<211> LENGTH: 20
<212> TYPE: DNA
<213> ORGANISM: Chlamydia trachomatis

<400> SEQUENCE: 3
cctgatgcta gggacggatt                                                20

<210> SEQ ID NO 4
<211> LENGTH: 21
<212> TYPE: DNA
<213> ORGANISM: Chlamydia trachomatis

<400> SEQUENCE: 4
ccctaaatta tgcggtggaa t                                              21

<210> SEQ ID NO 5
<211> LENGTH: 368
<212> TYPE: DNA
<213> ORGANISM: Chlamydia trachomatis

<400> SEQUENCE: 5 tcttttaaa cctccggaac ccacttcttc cacagattct tctaaagaac ctcctaaaga    60
atctgcatgg aaagtagtct ctcattctcg aggacgccgt cgcgctcgat ccaacccctc   120
ccctcacaca tctcaaaata ctccttctcc aaaagactct tctttagttg ctcgtacgga   180
taaagcggca acagatatct ttaattcggc taaacacaaa gcgattgaaa cgacaaaaag   240
aagtgatcag caaagcagat ccttacatat actgcacctt ttagctgaaa atccggaacc   300
cattgtgttc cactcagctc accaaacaaa ccacaacgat ccgcaaagaa tgctatgcga   360
tgccatcc                                                            368

<210> SEQ ID NO 6
<211> LENGTH: 462
<212> TYPE: DNA
<213> ORGANISM: Chlamydia trachomatis

<400> SEQUENCE: 6
cctgatgcta gggacggatt aaaaccttct cagcgacgta ttttatacgc tatgaaacaa    60
ttaaatctga ctccaggagt aaagcacaga aaatgcgcaa aaatttgcgg tgatacttcc   120
ggagattatc accctcatgg agaaagtgtc atttatccta ctttagtaag gatggcacag   180
gattgggcca tgcgataccc tcttgttgat ggtcaaggga attttggatc catcgacggg   240
gatccagctg ctgccatgcg atatacagag gctcgcctga ctcacagcgc tatcttttg    300 ttagaggacc tagataaaga tactgtagat atggtcccta actacgatga aactaaatat   360
gaacctgtag ttttttcttc aaaattcccc aatttacttt gtaatggctc ctcaggcatc   420
gcggtaggga tggcaacaaa tattccaccg cataatttag gg                     462
```